US005635482A

United States Patent [19]
Bhatnagar

[11] Patent Number: 5,635,482
[45] Date of Patent: *Jun. 3, 1997

[54] SYNTHETIC COMPOUNDS AND COMPOSITIONS WITH ENHANCED CELL BINDING

[75] Inventor: Rajendra S. Bhatnagar, Burlingame, Calif.

[73] Assignee: The Regents of the University of California, Oakland, Calif.

[*] Notice: The term of this patent shall not extend beyond the expiration date of Pat. No. 5,354,736.

[21] Appl. No.: 278,878

[22] Filed: Jul. 22, 1994

Related U.S. Application Data

[63] Continuation-in-part of Ser. No. 804,782, Dec. 9, 1991, Pat. No. 5,354,736, which is a continuation-in-part of Ser. No. 393,621, Aug. 14, 1989, abandoned.

[51] Int. Cl.⁶ .................. A61K 38/00; C07K 5/00; C07K 7/00
[52] U.S. Cl. ................. 514/14; 514/15; 514/16; 514/17; 514/18; 514/19; 530/345; 424/422; 424/423
[58] Field of Search ............... 514/12, 13, 14, 514/15, 16, 17, 18, 19; 530/345; 424/484–491, 422, 423, 435

[56] References Cited

U.S. PATENT DOCUMENTS

| | | | |
|---|---|---|---|
| 4,060,081 | 11/1977 | Yannas et al. | 128/156 |
| 4,992,226 | 2/1991 | Piez et al. | 264/109 |
| 4,994,081 | 2/1991 | Civerchia et al. | 623/5 |
| 5,007,934 | 4/1991 | Stone | 623/20 |
| 5,034,352 | 7/1991 | Vit et al. | 501/1 |
| 5,354,736 | 10/1994 | Bhatnagar | 514/14 |

OTHER PUBLICATIONS

Abstract from Poster Talk, Bhatnagar et al., "Collagen-Related Synthetic Peptides Promote Migration & Proliferation of Normal Neo-Natal Human Dermal Fibroblasts in Agarose Gels," *Am Soc Cell Biol Ann Mtg*, Dec. 1991.
Abstract from Poster Talk, Winkler et al., "Synthetic Peptides Inhibit T-Cell Attachment to Type I Collagen," *American Society of Cell Biology Annual Meeting*, Dec. 1991.
Abstract from Poster Talk, Qian et al., "Design of Biocompatible Materials: A Synthetic Analogue of Collagen," *American Academy of Implant Dentistry Foundation Research Symposium*, 1991.
Abstract from Poster Talk, Qian et al., "T-Cell Binding to Collagen is Inhibited by Synthetic Peptides," *Protein Society Meeting*, 1991.
Dessau et al., *Biochem. J.*, 169:55–59 (1978).
Kleinman et al., *J. Biol. Chem.*, 253:5642–46 (1978).
Gross, pp. 275–317 in Ramachadran et al., (eds), *Biochemistry of Collagen*, Plenum Press, New York (1976).
Miller et al., *Biochem.*, 15:787–92 (1976).
Kleinman et al., *Biochem. & Biophys. Res. Comm.*, 72:426–32 (1976).
Kleinman et al., *Analyt. Biochem.*, 94:308–12 (1979).
Silver, *J. Biol. Chem.*, 256:4973–77 (1981).
Dedhar et al., *J. Cell Biol.*, 104:585–93 (1987).
Pierschbacher et al., *J. Cell Biochem.*, 28:115–26 (1985).
Rudinger, pp. 1–7 in Parsons (ed.), *Peptide Hormones*, University Park Press, Baltimore (1976).
French et al., *Gene*, 39:311–312 (1985).
Bernard et al., *Biochemistry*, 22:5213–5223 (1983).
Wiengarter et al., *Biochemistry*, 24:6730–6734 (1985).
Fields et al., *J. Biol. Chem.*, 262(13):6221–6226 (1987).
Rantala–Ryhanen et al., *Eur. J. Biochem.*, 134:129–137 (1983).
Nagai et al., *Biochimica et Biophysica Acta*, 445:521–524 (1976).
Bicsak et al., *Arch. of Biochem. and Biophys.*, 242(1):256–262 (1985).
Green et al., *Tetrahedron Lett.*, 29(34):4341–4344 (1988).
Datta et al., *Proc. Natl. Acad. Sci. (USA)*, 84:393–397 (1987).
Shimotohno et al., *Proc. Natl. Acad. Sci. (USA)*, 82:3101–3105 (1985).
Yi et al., *Gene*, 36:241–247 (1985).
Sagata et al., *Proc. Natl. Acad. Sci. (USA)*, 82:677–681 (1985).
Schwartz et al., *Cell*, 32:853–869 (1983).
Van Het Schip et al., *J. Mol. Biol.*, 196:245–260 (1987).
Backhaus et al., *Gene*, 32:289–303 (1984).
Sodroski et al., *Science*, 225:421–424 (1984).
Abstract from Poster Talk, Bhatnagar et al., "Molecular Considerations in the Design of Collagen–Based Biomaterials," *Am. Acad. of Implant Dentistry Foundation Research Symposium*, 1991.
Yamada, *J. Biol. Chem.*, 266(20): 12809–12812 (1991).
Masui et al., *Biochemical Medicine*, 17:215–221 (1977).
*Peptides: Chemistry, Structure and Biology*, Proceedings of the Eleventh American Peptide Symposium, Jul. 9–14, 1989, La Jolla, California, edited by Rivier and Marshall, Leiden: Escom (1990), pp. 605–607.

*Primary Examiner*—Avis M. Davenport
*Attorney, Agent, or Firm*—Majestic, Parsons, Siebert & Hsue

[57] ABSTRACT

Compositions of the invention include composites comprising a biomaterial having compounds thereon with enhanced cell binding with respect to collagen. These composites are useful for soft and hard tissue repair or reconstruction and for in vitro uses. Suitable compounds with enhanced cell binding include synthetic peptides that mimic the conformation necessary for recognition and docking of collagen binding species (such as cell surface receptors for collagen and fibronectin) and have the amino acid residues -Ile-Ala- folded in a β-bend.

8 Claims, 2 Drawing Sheets

SYNTHETIC COMPOUNDS AND COMPOSITIONS WITH ENHANCED CELL BINDING

This invention was made with Government support under Grant No. AR-37267 awarded by the National Institute of Health. The Government has certain rights in this invention.

This is a continuation-in-part of Ser. No. 07/804,782, filed Dec. 9, 1991, now U.S. Pat. No. 5,354,736, which was a continuation-in-part of Ser. No. 07/393,621, filed Aug. 14, 1989 and now abandoned.

FIELD OF THE INVENTION

The present invention generally relates to compounds that mimic a small biologically active segment of collagen, and more particularly relates to compounds such as synthetic peptides that have enhanced cell binding with respect to collagen and that are usefully combined with matrices to form composites for growing vertebrate cells.

BACKGROUND OF THE INVENTION

Collagen is the most abundant protein found in vertebrates. Approximately 25 percent of all animal protein is collagen. Collagen is unusual among proteins in that the amino acid glycine constitutes one-third of the total amino acid content and occurs at nearly every third amino acid residue. Also, many proline amino acids are found in collagen. Collagen contains two amino acids present in very few other proteins, i.e., hydroxyproline and hydroxylysine. The sequence glycineproline-hydroxyproline recurs frequently.

Because glycine is a very small amino acid, chains of collagen can wind tightly around one another to form a triple helix. The side chains of proline form cross-links that lock the three strands together. Additionally, mature collagen frequently contains carbohydrate units covalently attached to its hydroxylysine residues. A disaccharide of glucose and galactose is commonly found attached to strands of collagen. Still other forms of collagen can form planar sheets, which are rich in carbohydrates. For a general description of the structure of collagen, see Stryer, Biochemistry (3d ed.), W. H. Freeman & Co., San Francisco (1988); Ramachandran et al. (eds.), Biochemistry of Collagen, Plenum Press, New York (1976); Mayne et al., (eds.), Structure and Function of Collagen Types, Academic Press, New York (1987).

Collagen functions as a structural protein of tissues. It is the major fibrous element in skin, cartilage, bone, tendon, teeth, and blood vessels. Collagen is present to some extent in nearly all organs and serves to hold cells together in discrete units. It forms insoluble fibers that have a high tensile strength. Furthermore, the basic structure of collagen is modified to meet the specialized needs of particular tissues, and these are reflected in the various types of collagen that have been identified.

The several types of collagen are a family of genetically related proteins that exhibit fundamentally similar secondary and tertiary protein structures, see, Mayne et al. (eds.), Structure and Function of Collagen Types, Academic Press, New York (1987). As used herein unless otherwise specified, "collagen" refers to any of the known types of collagens.

Type I collagen, the most prevalent type and the species found in skin, tendon, bone, and cornea, is comprised of two chains of one kind, termed $\alpha 1(I)$, and one of another, termed $\alpha 2(I)$. Other types of collagen have three identical chains. Each of the three strands consists of about 1,000 amino acid residues, and each has a helical conformation. The three strands wind around each other to form a superhelical cable and are hydrogen bonded to each other. As mentioned above, this structure is possible because of the presence and regularity of glycine units.

Studies have shown that the presence and concentration of imino residues, proline and hydroxyproline, are essential for generating and stabilizing the triple helical conformation of collagen, see Bhatnagar et al., pages 479–52 in Ramachandran et al. (eds.), Biochemistry of Collagen, Plenum Press, New York (1976); Bhatnagar et al., pages 429–38 in Agris (ed.), Biomolecular Structure and Function, Academic Press, New York (1978).

In short, the stability of the helical form of a single strand of collagen depends on the locking effect of proline and hydroxy-proline residues. The triple helix is further stabilized by transverse hydrogen bonding and van der Waals interactions between residues on different strands. The superhelix is sterically allowed because glycine occupies every third position in the amino acid sequence.

In addition to being a major determinant of the architecture and tensile strength of tissues, collagen participates in numerous physiologically important interactions. These include, but are not limited to, the formation of complexes with other macromolecules such as fibronectin, the modulation of cell proliferation, the mediation of cell migration and differentiation, and the modulation of specific gene expression.

In order for such interactions to occur, the molecules on the surface of collagen fibers must exhibit molecular perspectives that are specific for recognition. This requires local conformational changes. It has been suggested that the binding of certain cells, such as platelets, may involve a conformationally perturbed region of the $\alpha 1$ chain of collagen, which is located approximately one-quarter of the length of the chain from the C-terminus, see Dessau et al., Biochem. J., 169:55–59 (1978); Kleinman et al., J. Biol. Chem., 253:5642–46 (1978). This region also includes the only site known to be susceptible to proteolytic cleavage by the vertebrate enzyme, collagenase, see Gross, pages 275–317 in Ramachandran et al. (eds.), Biochemistry of Collagen, Plenum Press, New York (1976); Miller et al., Biochem., 15:787–92 (1976). Additionally, this region is known to be involved in the binding of fibronectin to collagen, see Dessau et al., Biochem. J., 169:55–59 (1978); Kleinman et al., Biochem. & Biophys. Res. Comm., 72:426–32 (1976); Kleinman et al., Analyt. Biochem., 94:308–12 (1979); and is also the site of intermolecular interactions leading to fibril formation, see Silver, J. Biol. Chem., 256:4973–77 (1981).

Previous studies have shown that the three amino acid sequence, Arg-Gly-Asp, found in a variety of proteins, including collagen, may play a major role in the binding of cells, see Dedhar et al., J. Cell Biol., 104:585–93 (1987); Pierschbacher et al., J. Cell Biochem., 28:115–26 (1985). This sequence appears twice within the $\alpha 1(I)$ chain, and one of those occurrences is within the conformationally perturbed region described above, see Kleinman et al., J. Biol. Chem., 253:5642–46 (1978).

Collagen fragments and synthetic peptide sequences corresponding to portions of collagen have been prepared and studied. Nagai et al. prepared eleven synthetic peptides by solution procedures to study substrate specificity of purified tadpole collagenase, with the synthesized peptides having the same or closely similar sequences to that occurring around the Gly-Ile bond in the position 772–773 of the $\alpha_1$ chain. The authors proposed an eight amino acid peptide (with acetyl at the N-terminus and esterified at the C-terminus) as the best substrate for vertebrate collagenase. Nagai et al., Biochimica et Biophysica Acta, 445, 521–524 (1976).

Collagen has been suggested in mixtures or combinations with bone minerals, such as is discussed in U.S. Pat. No. 4,992,226, inventors Piez et al., issued Feb. 12, 1991. Collagen has also been suggested in combination with hydrogels for cornea implants, as illustrated by U.S. Pat. No. 4,994,081, inventors Civerchia et al, issued Feb. 19, 1991. Skin and nerve tissue repairs have been suggested through use of endodermal implants and artificial epidermis fashioned out of collagen and mucopolysaccharide, as illustrated by U.S. Pat. No. 4,060,081, inventors Yannas et al., issued Nov. 29, 1977.

However, the present materials and composites presently employed or suggested as tissue implants or for tissue repair have various shortcomings. Collagen itself appears to cause some adverse reactions within the body. Also, the manner in which collagen is reconstituted during preparations of the combinations with bone minerals, hydrogels, and so forth, tends to markedly alter the normal collagen biological activity and apparently masks some of the biologically active sites.

SUMMARY OF THE INVENTION

In one aspect of the present invention, a family of synthetic peptides are provided that mimic the cell binding domain of collagen so that these compounds competitively inhibit the binding of cells to collagen by occupying the collagen receptors and also themselves bind to these receptors and can attach cells to various substrates, or matrices. The cell binding domain of these compounds has enhanced cell binding with respect to collagen. The domain includes a core sequence that, at physiologic conditions, is folded in a β-bend with the β-bend being formed at -Ile-Ala-. An illustrative synthetic peptide embodiment of the family has the amino acid sequence, Gly-Thr-Pro-Gly-Pro-Gln-Gly-Ile-Ala-Gly-Gln-Arg-Gly-Val-Val (SEQ ID NO:1). This fifteen amino acid embodiment has the same sequence as a particular, small region in the α1(I) chain of collagen. Another embodiment of the family includes six amino acid residues with the sequence Gln-Gly-Ile-Ala-Gly-Gln (SEQ ID NO:3). ID compounds of the invention mimic the conformation necessary for recognition and docking of collagen binding species (such as cell surface receptors for collagen and fibronectin).

Compounds of the invention may be carried by a matrix as a composite useful in growing cells. Such composites are preferably formed from biomaterials and have properties of promoting cell attachment to the matrix and promoting cell migration into the matrix when the matrix is porous. Among applications for composites of the invention are in reconstructive surgeries for hard and soft tissues, such as bone repair and tooth implants and ligament repair.

DETAILED DESCRIPTION OF THE INVENTION AND PREFERRED EMBODIMENTS

Novel synthetic compositions of matter are described in the present invention. These include compounds that are structurally or biologically analogous to a small region of collagen and mimic the conformation recognized by collagen binding species. The region from which synthetic peptides of the invention have been designed is sometimes referred to as "P-15", includes all or part of 15 amino acid residues, Gly-Thr-Pro-Gly-Pro-Gln-Gly-Ile-Ala-Gly-Gln-Arg-Gly-Val-Val, of the α1(I) chain of collagen, and spans approximately residues 766–780 of this chain. The P-15 region does not occur as a natural fragment of collagen nor is it a product of natural enzymatic cleavages. However, the coordinates defining the three-dimensional surface or shape that includes the presence of -Ile-Ala- in a β-bend conformation are given below. The surface or shape defined by these coordinates displays certain biological activities, which will be described more fully hereinafter. Very surprisingly, the dipeptide -Ile-Ala- itself displays 60% of the biological activity to that of P-15. This confirms that the -Ile-Ala- β-bend in the collagen analogues is critical to the biological activity, and indeed constitutes by itself an essential part of the inventive peptides.

Table 3 sets out the coordinates for the atoms in a structure defining the biologically active dipeptide -Ile-Ala- region. The coordinate computations were carried out using as a model compound, N-acetyl-isoleucyl-alanyl-methylamide (shown as SEQ ID NO:14 in Table 2). The coordinates of the area of interest begin with atom 7 (the nitrogen atom of isoleucine) and end with atom 34 (the carbonyl carbon of alanine).

Structures with substantially these same coordinates (by "substantially" is meant to include up to about a 15% variance) will generate the desired surfaces and display the biological activities described for the inventive peptides. The allowance for an amount of some variance is due to mobility and adaptability of fit between ligand and collagen receptor. Thus, such structures are considered to be within the definition of having the domain that mimics collagen bending to cells, or within the scope of including at least -Ile-Ala- folded in a β-bend at physiologic conditions, for purposes of this invention.

TABLE 3

| Atom No. | Residue | X | Y | Z |
| --- | --- | --- | --- | --- |
| 7 N | ILE 2 | 3.553 | 3.973 | 0.001 |
| 8 HN | ILE 2 | 2.730 | 4.556 | 0.001 |
| 9 CA | ILE 2 | 4.850 | 4.618 | 0.002 |
| 10 HA | ILE 2 | 5.373 | 4.383 | −0.925 |
| 11 CB | ILE 2 | 4.669 | 6.129 | 0.113 |
| 12 HB | ILE 2 | 4.086 | 6.489 | −0.735 |
| 13 CG2 | ILE 2 | 3.939 | 6.458 | 1.409 |
| 14 HG21 | ILE 2 | 4.522 | 6.099 | 2.257 |
| 15 HG22 | ILE 2 | 3.809 | 7.539 | 1.488 |
| 16 HG23 | ILE 2 | 2.964 | 5.974 | 1.409 |
| 17 CG1 | ILE 2 | 6.034 | 6.807 | 0.113 |
| 18 HG12 | ILE 2 | 6.557 | 6.571 | −0.813 |
| 19 HG13 | ILE 2 | 6.618 | 6.448 | 0.961 |
| 20 CD1 | ILE 2 | 5.853 | 8.318 | 0.224 |

TABLE 3-continued

| Atom No. | Residue | X | Y | Z |
| --- | --- | --- | --- | --- |
| 21 HD1 | ILE 2 | 5.332 | 8.555 | 1.151 |
| 22 HD2 | ILE 2 | 6.829 | 8.804 | 0.225 |
| 23 HD3 | ILE 2 | 5.270 | 8.679 | −0.623 |
| 24 C | ILE 2 | 5.698 | 4.142 | 1.172 |
| 25 O | ILE 2 | 6.923 | 4.212 | 1.124 |
| 26 N | ALA 3 | 5.042 | 3.655 | 2.228 |
| 27 HN | ALA 3 | 4.034 | 3.619 | 2.217 |
| 28 CA | ALA 3 | 5.736 | 3.171 | 3.404 |
| 29 HA | ALA 3 | 6.684 | 3.697 | 3.510 |
| 30 CB | ALA 3 | 4.909 | 3.401 | 4.663 |
| 31 HB1 | ALA 3 | 3.960 | 2.873 | 4.576 |
| 32 HB2 | ALA 3 | 5.453 | 3.028 | 5.530 |
| 33 HB3 | ALA 3 | 4.722 | 4.469 | 4.784 |
| 34 C | ALA 3 | 6.015 | 1.677 | 3.300 |
| 35 O | ALA 3 | 6.562 | 1.079 | 4.225 |

Collagen exists in a very tightly coiled superhelical structure, wherein its tensile strength is stabilized by the high content of imino residues. Thus, for interactions with other cells or compounds, the collagen structure must be perturbed. Thermal motion can overcome the forces that stabilize the triple-stranded helix, yielding a disrupted structure. An advantage of the present invention is that, given the size and structure of the synthetic compositions disclosed herein, there is no need for such conformational perturbations. Compounds of the invention not only can mimic the biological activity of collagen, but also can exhibit cell binding functions enhanced with respect to collagen. The amino acid sequences of synthetic peptides in accordance with the invention need not correspond precisely to the P-15 region, but rather may include (indeed, sometimes preferably only include) a portion of it.

The P-15 region represents half of one turn of the collagen triple helix, i.e. fifteen residues, which is believed to be exposed in intact collagen molecules on the surface of fibers. The other half of the turn faces the core of the fiber. Theoretical and experimental studies showed that the sequence contained in P-15 can acquire a conformation dramatically different from the triple helical conformation generally observed in the rest of the collagen molecule. This atypical, or "non-collagen", conformation is believed necessary for recognition by and the docking of collagen binding species, such as cell surface receptors for collagen and fibronectin. The three dimensional surface presented by the P-15 region or parts of the P-15 region is complementary to the reactive surface present on the binding species (receptors, fibronectin). Compounds of the invention mimic this surface of collagen, and any compounds that can generate a similar surface can be expected to have similar biological activity.

An embodiment of the present invention involves synthetic compositions that have a biological activity functionally comparable to that of all or some portion of P-15. By "functionally comparable," is meant that the shape, size, and flexibility of a compound is such that the biological activity of the compound is similar to the P-15 region, or a portion thereof. Biological activities that may be possessed by the peptide include inhibition of collagen synthesis, inhibition of collagen binding, and inhibition of cell migration. Of particular interest to the present invention is the property of enhanced cell binding. Useful compounds should be selected on the basis of similar spacial and electronic properties as compared to P-15 or a portion thereof. These compounds typically will be small molecules of 100 or fewer amino acids or in the molecular weight range of up to about 5,000 daltons, more typically up to 2,500 daltons. Inventive compounds will be illustrated with synthetic peptides; however, nonpeptides mimicking the necessary conformation for recognition and docking of collagen binding species are also contemplated as within the scope of this invention. For example, cyclic peptides on other compounds in which the necessary conformation is stabilized by nonpeptides (e.g., thioesters) is one means of accomplishing the invention.

It is the central portion, forming a core sequence, of the P-15 region that is essential for the desired collagen-like activity. Thus, peptides of this invention may contain the sequence Gly-Ile-Ala-Gly (SEQ ID NO:9). The two glycine residues flanking the fold, or hinge, formed by -Ile-Ala- are hydrogen bonded at physiologic conditions and thus stabilize the Q-fold. Because the stabilizing hydrogen bond between glycines is easily hydrolyzed, two additional residues flanking this sequence can markedly improve the cell binding activity by further stabilizing the bend conformation. For example, addition of glutamine at each end, as represented by Gln-Gly-Ile-Ala-Gly-Gln (SEQ ID NO:3) markedly improves the activity and is a synthetic peptide of this invention. In fact, this six amino acid (SEQ ID NO:3), is as active, or more active, than a peptide having the entire P-15 region. A nonapeptide Gly-pro-Gln-Gly-Ile-Ala-Gly-Gln-Thr (SEQ ID NO:2) is also equally as active as the entire P-15 region. On the other hand, if there is cleavage in the middle of the Gly-Ile-Ala-Gly active site, activity is lost.

A number of synthetic peptides of the family in accordance with this invention have been prepared and are shown in Table 1.

TABLE 1

| Inventive Peptides | SEQ ID NO: |
| --- | --- |
| Gly—Thr—Pro—Gly—Pro—Gln—Gly—Ile—Ala—Gly—Gln—Arg—Gly—Val—Val | 1 |
| Gly—Pro—Gln—Gly—Ile—Ala—Gly—Gln—Arg | 2 |
| Gln—Gly—Ile—Ala—Gly—Gln | 3 |
| Gln—Gly—Ile—Ala—Gly—Gln—Arg | 4 |
| Phe—Gly—Ile—Ala—Gly—Phe | 5 |
| Gly—Ile—Ala—Gly—Gln | 6 |
| Gln—Gly—Ala—Ile—Ala—Gln | 7 |

Although SEQ ID NO:6 has only five amino acid residues, it has a cell-binding activity (relative to the SEQ ID NO:1 peptide) of 70%. However, another five amino acid peptide prepared (Gln-Gly-Ile-Ala-Gly (SEQ ID NO:8)) only had a cell-binding activity relative to the SEQ ID NO:1 peptide of 42%, which means it is slightly enhanced with respect to collagen, but not significantly enhanced.

The synthetic peptide identified in Table 1 as "SEQ ID NO:7" differs from the other family members in having the essential -Ile-Ala- hinge flanked by alanine and glutamine, respectively. This is believed due to the formation of a hydrogen bond between the alanine and glutamine that stabilizes the essential β-fold.

In theoretical studies those peptides having the SEQ ID NO:1, SEQ ID NO:2, and SEQ ID NO:3 showed a high potential for a conformation in which the peptide is folded in a β-bend at the -Ile-Ala- portion. Solution conformations in a variety of membrane-mimetic environments showed that a folded sheet-like structure is generated by these peptides. As the side chains of Gln retain hydrophobic character, a stabilizing interaction ensues and the bend structure is stabilized. This concept was confirmed by synthesizing the hexapeptide having the SEQ ID NO:5 as an analogue, which exhibited cell binding activity comparable to that of the peptides of SEQ ID NO:1, 2, and 3. Thus, the molecular shape and stabilizing interactions are critical for the desired activity. The importance of the residues -Ile-Ala- as the β-bend of the core sequence is emphasized by the lack of activity in a peptide analogous to the peptide of SEQ ID NO:7, but with Ala of the -Ile-Ala- bend replaced by Gly.

Several more synthetic peptides were prepared and tested for cell binding activity (relative to the SEQ ID NO:1 peptide) all of which have the β-bend feature and which have excellent cell binding activity. These are shown in Table 2.

TABLE 2

| Inventive Peptides | SEQ ID NO: |
|---|---|
| Phe—Gly—Ile—Ala—Gly—Phe | 9 |
| Cys—Gly—Ile—Ala—Gly—Cys | 10 |
| Glu—Gly—Ile—Ala—Gly—Lys | 11 |
| NAc—Ile—Ala—Ala | 12 |
| Ile—Ala—βAla | 13 |
| NAc—Ile—Ala—N—Me | 14 |

To briefly summarize, synthetic peptides of this invention must have a core sequence that has -Ile-Ala- formed in a β-bend at physiological conditions. This β-bend of the core sequence means that the domain of the inventive synthetic peptides has an ability to exist in that conformation, either due to allosteric induction, or interaction, or more preferably by sufficient flanking amino acid residues to substantially stably hold the bend, such as by flanking hydrogen bonded residues. Additional flanking amino acid residues, up to a total of about 15, if present, will typically together comprise a domain that is inhibitory of collagen bonding to cells and that has enhanced cell binding with respect to collagen. The flanking moieties may facilitate the "presentation" of the β-fold conformation in receptor situations. However, as earlier noted, the -Ile-Ala- dipeptide itself is quite active. Because of the enhanced cell binding property for synthetic peptides of this invention, cell attachment is promoted. Additional amino acid residues or other moieties may be added to one or the other side of this domain to facilitate coupling or the like, so long as the essential cell-binding property of the domain is not substantially inhibited.

Synthetic compounds of this invention also have one or more of the following properties: they promote cell migration into porous lattices; they bind to collagen receptors; they induce metalloproteinases; they can down-regulate prolyl hydroxylase and collagen; they inhibit cell binding to collagen; and they inhibit cell migration in vitro. The enumerated properties (including promotion of cell attachment) of synthetic peptides for the inventive family can be utilized to convey these highly desirable properties to composites for a wide variety of uses. The down-regulation of prolyl hydroxylase is of particular interest because it represents a key step in collagen synthesis. This means that compounds of the invention can be used as inhibitors of collagen synthesis to block formation of scar tissue and thus promote scarless healing.

Synthetic peptides of the inventive family are preferably substantially free of the following: glycosylation, association with other peptide chains, crosslinking, and hydroxylation, which tend to be present in naturally occurring collagen. By "substantially free," it is meant less than the average amount found in naturally occurring collagen. Peptides of the invention are preferably also substantially free of blocking groups (often used during peptide synthesis), such as t-butyloxycarbonyl group ("BOC").

Synthetic peptides that have the desired biological activities may be produced by either of two general approaches.

Polypeptides having fewer than about 100 amino acids, usually fewer than about 50 amino acids, and more usually fewer than about 25, may be synthesized by the well-known Merrifield solid-phase chemical synthesis and modifications thereof method wherein amino acids are sequentially added to a growing chain, see Merrifield, J. Am. Chem. Soc., 85:2149–56 (1963). Linear peptides may be chemically synthesized by manual means or by automation in commercially available synthesis equipment. Systems for manually synthesizing peptides on polyethylene pegs are available from Cambridge Research Biochemicals, Cambridge, Mass. Automatic peptide synthesis equipment is available from suppliers, including Applied Biosystems, Inc., Foster City, Calif.; Beckman Instruments, Inc., Waldwick, N.J.; and Biosearch, Inc., San Rafael, Calif. Using such automatic synthesizers according to manufacturer's instructions, peptides may be produced in gram quantities for use in the present invention.

Since the use of relatively short, linear peptides is advantageous in performing the methods of use described in the present invention, the peptides are preferably produced in quantity, and will be free from contaminating substances, which are often found in peptides produced by recombinant techniques.

However, the synthetic peptides of the present invention may be synthesized by recombinant techniques involving the expression in cultured cells of recombinant DNA molecules encoding the gene for a desired portion for the α1(I) strand of collagen. The gene encoding the desired portion of the α1(I) strand of collagen itself may be natural or synthetic. Conveniently, polynucleotides may be synthesized by well-known techniques. For example, short single-stranded DNA fragments may be prepared by the phosphoramidite method described by Beaucage et al., Tetrahedron Letters, 22:1859–62 (1981). A double-stranded fragment then may be obtained either by synthesizing the complementary strand and annealing the strands together under appropriate conditions or by adding the complementary strand using DNA polymerase with an appropriate primer sequence. The natural or synthetic DNA fragments coding for the desired portion of the α1(I) strand of collagen will be incorporated in DNA constructs capable of introduction to and expression in an in vitro cell culture.

Usually, the DNA constructs will be suitable for replication in a unicellular host, such as yeast or bacteria, but also may be intended for introduction and integration within the genome of cultured mammalian or other eukaryotic cell lines. DNA constructs prepared for introduction into bacteria or yeast will include a replication system recognized by the host, the DNA fragment encoding for the desired α1(I)

polypeptide, transcriptional and translational initiation regulatory sequences joined to the 5'-end of the α1(I) collagen DNA sequence, and transcriptional and translational termination regulatory sequences joined to the 3'-end of the α1(I) collagen sequence. The transcriptional regulatory sequences will include the replication system and transcriptional and translational regulatory sequences, together with an insertion site for the α1(I) collagen DNA sequence, may be employed.

For use in cell binding, these peptides are obtained in a substantially pure form, that is, typically about 50% w/w or more purity, substantially free of interfering proteins and contaminants. Preferably, the peptides are isolated or synthesized in a purity of at least about 80% w/w and, more preferably, in at least about 95% w/w purity. Using conventional purification techniques, homogeneous peptides of at least 99% w/w can be obtained. For example, the peptides may be purified by use of reverse-phase high performance liquid chromatography. Usually, however, it is not essential to obtain highly pure, i.e., 99% peptides when using these peptides to bind cells.

Identification of useful compounds having the necessary size, shape and three-dimensional structure for the collagen mimicking properties of this invention can be performed through the use of techniques known to those working in the area of drug design. Such methods include, but are not limited to, self-consistent field (SCF), configuration interaction (CI), and normal mode dynamics computer programs, all of which are readily available. See Rein et al., Computer-Assisted Modeling of Receptor-Ligand Interactions, Alan Liss, New York (1989). For example, amino acid substitutions of the P-15 region (other than those already tested and shown acceptable) can be performed and the active peptides screened by simple collagen inhibition methods described hereinafter. Preparation of identified compounds will depend upon the desired characteristics of the compounds and will involve standard chemical synthetic techniques, see Carey et al., Advanced Organic Chemistry, Part B, Plenum Press, New York (1983).

In yet another embodiment, monoclonal antibodies may be raised against an epitopic region defined by P-15 or a portion thereof, or by any of the compounds of the present invention, wherein the epitopic region is responsible for binding and biological activity. By then raising antibodies against the first antibody, the binding region of the anti-idiotypic antibodies may provide functional analogs of P-15, or a functionally similar compound.

Such antibodies may be obtained by injecting the purified analog into a wide variety of vertebrates in accordance with conventional techniques. Suitable vertebrates include mice, rats, sheep, and goats; in particular, mice. Often, the animals are bled periodically with successive bleeds having improved titer and specificity. The compound may be injected intramuscularly, intraperitoneally, subcutaneously, or the like. Often, a vehicle is employed, such as a complete or incomplete Freund's adjuvant. If desired, monoclonal antibodies can be prepared. Alternatively, the compound may be used to isolate monospecific antibodies from a natural source.

To obtain monoclonal antibodies, spleen cells from the immunized vertebrate are immortalized. The manner of immortalization is not critical. Presently, the most common method is fusion with a myeloma fusion partner. Other techniques include EBV transformation; transformation with bare DNA, e.g., oncogenes, retro-viruses, etc.; or any other method that provides for stable maintenance of the cell line and production of monoclonal antibodies. Human monoclonal antibodies may be obtained by fusion of the spleen cells with an appropriate human fusion partner. A detailed technique for producing mouse×mouse monoclonal antibodies is taught by Oi et al., pages 351–72 in Mishell et al. (eds.) Selected Methods in Cellular Immunology, W. H. Freeman & Co., San Francisco (1980). The antibodies of the present invention may be from any immunoglobulin class.

The present invention also includes composites and methods of use for promoting vertebrate cell adhesion comprising attaching any of the above-described compositions of matter to a substrate (that is, a matrix) and adding cells to the composite. Substrates include, but are not limited to, glass, plastics, hydroxyapatite, ceramics, organic polymers (resorbable and non-resorbable), metallics, gels, particulate and coating salts such as calcium phosphate, and silica. Particularly preferred substrates are biomaterials, that is, are biologically compatible for in vivo applications and for cell culture in vitro. Preferred types of cells to be adhered include fibroblasts; however, most, if not all, cell types may be used.

The mode of attachment can be via covalent linkages, noncovalent interactions, or nonspecific adsorption. Covalent linkages include, but are not limited to, those involving ester, amide, or ether, see Carey et al., Advanced Organic Chemistry, Part B, Plenum Press, New York (1983). An exemplary method of covalent linkages involves peptides of the present invention with additions of nonnatural amino acids at either the N-terminus or C-terminus to provide for binding or conjugation of the peptide to a solid phase or another protein. For example, a cysteine sequence may be added to either terminus to facilitate coupling to a carrier. Hydrophobic residues or lipid-containing moieties, such as amino acids containing hydrophobic side chains, may be added to enhance liposome or membrane binding. When the necessary domain includes other noninterfering moieties or spacer arms (such as to facilitate binding) then the overall size of the cell attaching compound, or peptide, will usually be increased to greater than 15 amino acids of the P-15 region.

The substrate of choice may be pretreated with CNBr or other activating reagents to facilitate coupling of the composition to the substrate. Noncovalent interactions and nonspecific adsorption typically would involve the direct application of a solution containing the present compositions to the substrate. These methods of use have many applications, e.g., culturing cells to study their physiology and to make specific compounds, etc.

Particularly envisioned applications for composites of the invention are orthopedic applications such as bone filling/fusion for osteoporosis and other bone diseases, cartilage repair for arthritis and other joint diseases, and tendon repair. For soft tissue repair, the following applications are envisioned: nerve repair, organ repair, skin repair, vascular repair, muscle repair, and ophthalmic applications.

A few examples will be more fully described hereinafter with other uses and advantages being readily apparent to one of ordinary skill in the art. The following examples are intended to be merely illustrative of the present invention and are not to be read as limiting.

Example 1 demonstrates the enhanced promotion of cell adhesion by an inventive peptide (SEQ ID NO:1) that is coextensive with the P-15 region, as compared with collagen. Example 2 illustrates comparative inhibition of cell binding to collagen in the presence of the same inventive peptide (SEQ ID NO:1), and compared also with other (non-inventive) peptides. Example 3 illustrates properties of the embodiment with agarose gel, and shows that fibroblast cells placed on top of agarose gel not only grew, but actually migrated into the gel itself and displayed a morphology reminiscent of cells in tissues. Example 4 illustrates use of the invention with coated hydroxylapatite particles incorporated into an agarose gel. Fibroblasts placed on the surface of the agarose gel grew into the gel and organized on and around the coated particles in tissue-like masses. Example 5 illustrates substantially nonporous beads coated with the invention on which fibroblasts cells cover the bead surfaces and start forming cell networks. Example 6 illustrates covalently bonded inventive peptide (SEQ ID NO:1) to polyglycolide fibers.

EXAMPLE 1

The peptide Gly-Thr-Pro-Gly-Pro-Gln-Gly-Ile-Ala-Gly-Gln-Arg-Gly-Val-Val (SEQ ID NO:1) of the present invention was synthesized by solid phase procedures using symmetrical anhydrides for coupling of Boc-amino acids, except for Q residues that were coupled with 1-hydroxybenzyl triazole. Circular dichroism and $^1$H and $^{13}$C NMR studies suggest that the peptide exists in a random conformation in aqueous solutions and has little tendency to generate collagen or polyproline-like conformations in solution in the presence of helicogenic solvents, but shows a tendency to form a β-strand structure in decteasingly polar solvents.

All media and supplies for tissue culture were obtained from University of California San Francisco Tissue Culture Facility. Cycloheximide was purchased from Sigma Biochemicals, St. Louis, Mo. Rat tail tendon collagen was purified to homogeneity and characterized in our laboratory using published methods. Tissue culture dishes (35 mm diameter, Falcon Plastics) were coated with collagen dissolved in 0.01N acetic acid to a concentration of 10 µg/ml. The dishes were allowed to air dry overnight under ultra-violet light to maintain sterility.

Primary cultures of fibroblast cells from 19-week fetal human dermis were obtained. The cultures were maintained in Eagles minimum essential medium with Earle's salts supplemented with 10% fetal bovine serum. All cells used were in the second passage and were obtained from confluent cultures. Prior to release and dispersion with trypsin, the cells were rinsed three times with phosphate buffered saline. The cell layers were exposed for two minutes to 0.05% trypsin, 0.02% NaEDTA in phosphate buffered saline, and rinsed with serum free medium.

Glass coverslips (12–15) were washed in a cleaning solution overnight then rinsed with large amounts of distilled water. The coverslips were then sterilized by drying between sheets of filter paper in an oven at high temperature. The coverslips were then placed in small culture dishes under sterile conditions. A solution of collagen in acetic acid (1 mg/ml) was prepared. Fifty microliters of solution was placed on each of four coverslips, which were then dried in air overnight. A solution of the peptide in acetic acid (1 mg/ml) was prepared. Four coverslips were treated with 50 µl of the solution and then dried as described above.

Approximately 100,000 fibroblast cells were pipetted onto four control coverslips and dishes, four collagen coated coverslips and dishes, and four peptide coated coverslips and dishes. After 15 minutes, excess medium containing floating cells was removed from each dish. Fresh medium was added and the dishes were examined under a microscope to determine the extent of binding of cells to the respective coverslips. If the number of bound cells appeared to be different, an assay for DNA in the cells attached to each coverslip was performed. The cells were counted using a hemocytometer.

RELATIVE BINDING OF CELLS AFTER 15 MINUTES

|  | Concentration of Cells |
|---|---|
| Control (no collagen or peptide) | 7.01 |
| Collagen | 8.59 |
| Inventive Peptide (SEQ ID NO: 1) | 11.05 |

These results demonstrate an increase of 60% in cell binding of the inventive peptide over the control (no collagen or peptide) dishes and an increase of 40% in cell binding of the inventive peptide over collagen-coated dishes.

In various other similar studies the sequence 1 peptide has been shown to be at least twice as potent as collagen in binding cells to glass or to polystyrene. Consequently, all the synthetic peptides listed in Table 2, below, had significantly enhanced cell binding with respect to collagen (whereas, the earlier discussed SEQ ID NO:8 and SEQ ID NO:9 peptides, although having some biological activity, were not significantly enhanced with respect to collagen).

EXAMPLE 2

Collagen related, but non-inventive peptides, (Pro-Pro-Gly)$_{10}$ and (Pro-Hyp-Gly)$_{10}$ (wherein Hyp is hydroxyproline), were obtained from Peninsula Laboratory, Belmont, Calif. Polyproline was purchased from Sigma Biochemicals, St. Louis, Mo. Dynorphin 1-13 and human preangiotensinogen 1-14 were purchased from Bachem, Torrance, Calif. Three different fibronectin related peptide sequences were also obtained from Bachem and were used without further analysis.

The inventive peptide (SEQ ID NO:1) was synthesized as described in Example 1 and the same procedures and conditions of Example 1 were used herein.

In this experiment to examine the effect of various additives on binding, the additives were added in the medium containing the cells before being transferred to the dishes for the binding assay. It was observed that cell binding to collagen proceeds rapidly in the beginning of the experiment but then slows down after approximately 30 minutes and approximately 70–80% of the cell binding in the absence of a peptide occurs during this time. The effect of the peptide inhibitor on the initial rate of the binding reaction between cells and collagen was examined. The effects of various conditions on cell binding to collagen after 30 minutes were usually compounded.

The inhibition of cell binding by the inventive peptide was specific for the peptide, because a number of other peptides failed to show the same effect, see results presented below. In order to ascertain if inhibition of binding by peptides may be a nonspecific process, the effect of equimolar concentrations ($35 \times 10^{-6}$M) of several peptides on the binding of cells to collagen was compared. All peptides used had small inhibitory effects on cell binding, although none reached the level of inhibition observed with the inventive peptide. As seen in the results, polyproline, (PPG)$_{10}$ and (P-Hyp-G)$_{10}$, peptides with collagen-related conformations, did not significantly affect the binding of cells. Under the conditions of these experiments, polyproline and (PPG)$_{10}$ exist as single chains in polyproline conformation whereas (P-Hyp-G)$_{10}$ is a triple helix. The behavior of dynorphin 1-13 and preangiotensinogen 1-14, peptides similar in size to the inventive peptide, on cell binding was also examined. They did not affect the binding of cells to collagen to the extent shown by the inventive peptide. These results show that the inventive peptide is a potent inhibitor of the binding of cells to collagen.

EFFECT OF AN INVENTIVE PEPTIDE AND OTHER PEPTIDES ON THE ATTACHMENT OF CELLS TO COLLAGEN SUBSTRATES

|  | % of Maximal Maximal Cell Attachment | % Inhibition of Cell Attachment |
|---|---|---|
| Control (no addition) | 100 | — |
| Inventive, 7.2 × 10$^{-6}$M | 15 | 85 |
| Inventive, 36 × 10$^{-6}$M | 12 | 88 |
| (PPG)$_{10}$$^a$, 35 × 10$^{-6}$M | 79 | 21 |
| (P—Hyp—G)$_{10}$$^b$, 35 × 10$^{-6}$M | 87 | 13 |
| Polyproline$^c$, 1.7 × 10$^{-6}$M | 90 | 10 |
| Dynorphin 1–13, 35 × 10$^{-6}$M | 81 | 19 |
| Preangiotensinogen 1–14, 35 × 10$^{-6}$M | 88 | 12 |

$^a$Under the conditions of this experiment, (Pro—Pro—Gly)$_{10}$ is not a triple helix. (T$_m$ in H$_2$O is 24.5° C.)
$^b$Under the conditions of this experiment, (Pro—Hyp—Gly)$_{10}$ is a triple helix.
$^c$MW approx. 2,700 kilodaltons.

The relative efficiencies of some synthetic peptides of this invention for cell-binding activity (relative to the inventive peptide illustrated in Examples 1 and 2) are set out in Table 4.

TABLE 4

| | SEQ ID NO: | Relative Cell-Binding Activity |
|---|---|---|
| Gly—Pro—Gln—Gly—Ile—Ala—Gly—Gln—Arg | 2 | 100 |
| Gln—Gly—Ile—Ala—Gly—Gln | 3 | 120 |
| Gln—Gly—Ile—Ala—Gly—Gln—Arg | 4 | 60 |
| Phe—Gly—Ile—Ala—Gly—Phe | 5 | 87 |
| Gly—Ile—Ala—Gly—Gln | 6 | 70 |
| Gln—Gly—Ala—Ile—Ala—Gln | 7 | 70 |

EXAMPLE 3

Figure 1:
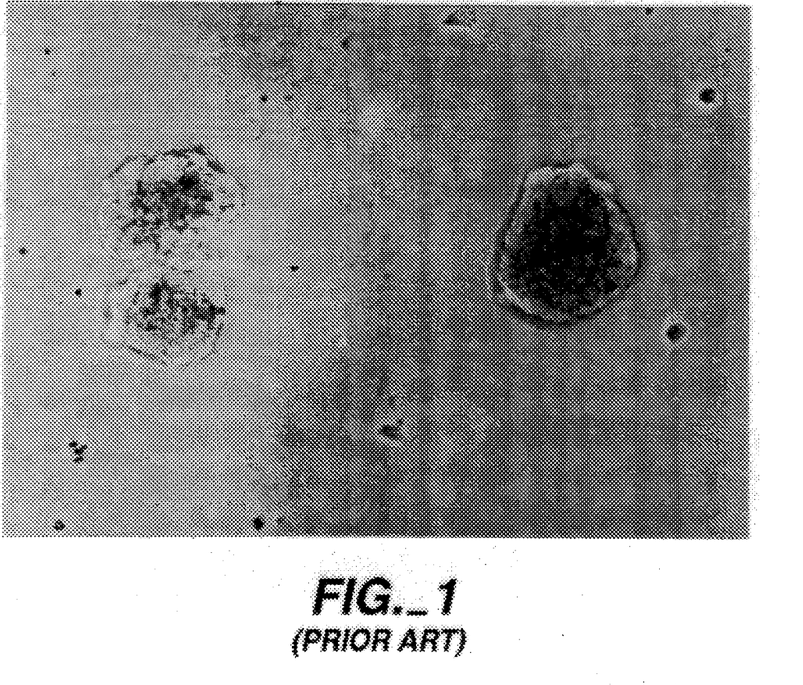
FIG. 1 is the photograph of an agarose gel on which fibroblast cells were placed and after 24 hours died. The agarose gel on which the cells were placed was a prior art gel.
Figure 2:
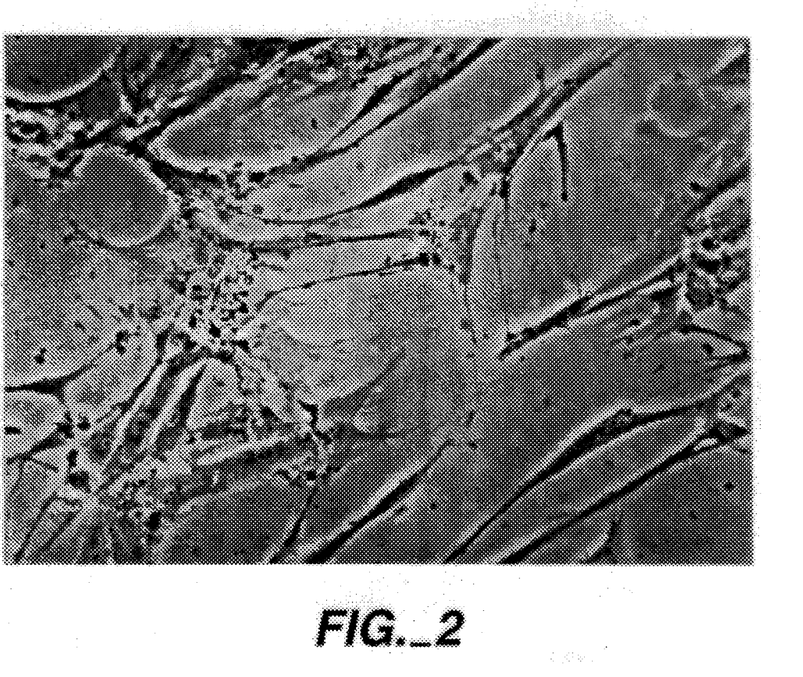
FIG. 2 is the photograph of an inventive embodiment in which an agarose gel included an inventive peptide. Fibroblast cells were placed on the gel surface, and commenced to grow and to migrate into the gel itself.

Referring to FIGS. 1 and 2, a prior art agarose gel was prepared with an agarose concentration of 2 mg/ml and between 100,000–200,000 fibroblast cells were placed on the gel surface. The agarose gel had been prepared with a suitable fibroblast cell growth medium and the cells placed on the agarose gel were treated with growth medium; however, the cells died within 48 hours, as is illustrated by the FIG. 1 photograph. By contrast, when 100 µg of the SEQ ID NO:1 peptide was included in an otherwise analogous preparation of agarose gel and fibroblast cells were again placed on top, then the cells not only grew, but actually migrated into the gel itself, as is illustrated by the FIG. 2 photograph taken 72 hours after plating. This was quite surprising because cells normally do not migrate well into gels. The fibroblasts that grew in the inventive gel medium displayed a morphology reminiscent of cells in tissues. The fibroblast population continued to grow rapidly until cells filled the lattice of the gel. These fibroblasts appear to be oriented in ordered arrays and exhibited marked biosynthetic activity.

Different concentrations of the inventive peptides in hydrogels were studied. Less than about 50 µg/ml was found to lead to not very efficient cell growth and migration into the gel. Greater than about 200 µg/ml provided results about comparable to that obtained in about 50 µg/ml to about 100 µg/ml concentration range. Different types of cells appear to prefer different inventive peptide concentrations in hydrogels, probably due to differences in receptor densities, but in general about 100 µg/ml will be effective.

Composites of the invention are particularly useful in growing cells, as they include a compound that promotes cell attachment (that is, the compound promotes cell binding in a manner similar to that of collagen, but where the cell binding is enhanced with respect to collagen). Composites of the invention are prepared by associating the cell attachment promoting compound, such as the synthetic peptides earlier described, to a matrix. Because the synthetic peptides define a domain that mimics the cell binding domain of collagen and that has enhanced cell binding with respect to collagen, a number of applications become possible, and matrices useful in forming composites of the invention can take a variety of physical and chemical forms.

For one example, the matrix can be inert, solid and non-porous, such as known and presently used as vessels for cell culture. When such cell culture vessels (petri dishes, flasks and so forth), typically formed of polystyrene or glass, have the cell binding peptides adsorbed or grafted on the surfaces to be exposed to cells, then these treated vessels can be used for tissue culture. The treated vessels have the advantage of anchoring cells with a compound simulating their natural ligand, unlike other materials now used for coating cell culture dishes. It is well-known that the differentiation and behavior of cells is modulated by their interaction with their natural extracellular matrix. Since the cell binding peptides of this invention are analogues of, or mimic, collagen, they elicit substantially the same response in cells as does collagen itself. The attachment of cells to such treated vessels is markedly greater than on uncoated surfaces or for surfaces coated with gelatin or even when coated with collagen itself.

Another form that may be taken by matrices of this invention is that of soluble polymers. When cell binding peptides of this invention are carried, or bound to, soluble polymers, then cells can be cultivated in large masses. Because these cultures float in the medium, they are constantly bathed in the medium and have continuous contact with nutrients and additives. Thus, the desired secretory products of the cells can be easily recovered from the medium.

Other suitable matrices for practice of this invention include various polymers and hydrogels. Such composites are useful in constructing templates for repair of soft tissue, for rapid replacement of lost tissue, and for reconstructive and plastic surgery.

Composites of this invention formed with hydrogels as the matrix promote the influx of cells. It is well known that cells differentiate to a greater extent in a three dimensional environment in contact with the surrounding extracellular matrix. Since synthetic peptides of this invention mimic collagen, cells in inventive composites, where the matrices are hydrogels, behave as if the cells are surrounded by extra-cellular matrix and undergo differentiation. Also for soft tissue repairs, the gels can be injected prior to gelation and then the gel formed in situ.

Composites of the invention can thus be made with resorbable polymers of various kinds, having peptide grafted onto the lattice of the polymeric material. Of course, polymeric supports that are limited in resorbable properties such as hydroxyethyl methacrylate, polymethylmethacrylate, and N-vinylpyrrolidone methylmethacrylate, as a few examples, are also feasible. The composites can then be implanted in the tissue defect. (By "grafting" of peptide so as to be carried by or bound to the matrix is meant the various modes of attachment earlier described.)

Among the known and suitable resorbable hydrogels are combinations of polylactacte and polyglycollate. Compounds of the invention can be covalently bound to such materials during synthesis of the polymers themselves or the polymers can be hydrolyzed such that attachment sites are available by irradiating the polymer or by chemically activating the polymer to generate free radicals. Then conventional techniques for grafting, or immobilizing, peptides onto polymer supports can be utilized to prepare inventive composites. Resorbable hydrogels or polymers so prepared are particularly useful for soft tissue reconstructions. For hard tissue reconstructions or repair (e.g., bone repair) it is desirable to combine such water soluble, or resorbable, polymer species with a bioceramic, such as for example bioglass, aluminum oxide, calcium aluminate, tricalcium phosphate, and hydroxyapatite.

Matrices of the invention can also be porous, and in bead, particulate, or fibrous forms. For example, calcium phosphate materials, such as apatite-based ceramics, have been suggested for producing porous tissue implants or prosthesis materials with micropores sufficient to permit tissue attachment. It is true that hydroxylapatite itself has a limited ability to promote cell attachments; however, inclusion of inventive compounds markedly increases the ability of cells to attach, as is illustrated by Example 4.

EXAMPLE 4

Particulate hydroxylapatite was obtained from CeraMed Corporation of Lakewood, Colo. under the designation "osteograph." Particles were coated by preparing a 100 µg/ml solution of inventive peptide (SEQ ID NO:1) in PBS into which 10 µg of the hydroxylapatite product was dispersed and allowed to sit overnight. The thus coated particles were then incorporated into an agarose gel that either had (a) inventive peptide therein (as described for the FIG. 2 photograph) or had (b) no inventive peptide (as described for the FIG. 1 photograph). Fibroblasts were placed on the surfaces of these gels. Where the particles were coated but the gel did not include inventive peptide (inventive composition (b)), then the cells migrated into the gel to the particles and formed spreading colonies which tended to clump. Where the coated particles were in a gel that also included inventive peptide (inventive composition (a)), there was a very large influx of cells into the gel that organized on and around the coated particles in tissue-like masses.

By contrast, when uncoated particles were included into a prior art agarose gel, a few cells did attach, but at about a ten fold reduction with respect to inventive composition (b).

The osteograph (hydroxylapatite) product, when reconstituted with PBS, is presently used for periodontal repair. As can be readily appreciated, forming an inventive composite with such hydroxylapatite will provide a significantly improved composition for tissue repair.

EXAMPLE 5

In a manner analogous to that described in Example 4, dense beads of hydroxylapatite (substantially nonporous) have been coated with inventive peptides. Fibroblast cells covered the bead surfaces and have been observed to start "budding" together and forming networks of cells.

EXAMPLE 6

The inventive peptide embodiment (SEQ ID NO:1) was chemically bonded to reactive groups generated on a fiber surface by limited ester-bond cleavage. The fibers were composed of polyglycolide (of the polyester class). The bonding was accomplished as follows. The fibers were washed with 0.1N NaOH for about 1½ minutes to cleave some of the ester bonds so that carboxyl and hydroxyl groups were formed as active potential linking moieties on the fiber surfaces. The inventive peptide was then coupled in water soluble carbodiimide to cause covalent bonding. Approximately 70 µg peptide/g polyglycolide was covalently linked. In a manner such as described, control fibers were identically treated but were grafted with glycine instead of the SEQ ID NO:1 inventive peptide.

The treated fibers were then placed in agarose-coated dishes (the dishes were agarose coated to prevent binding of cells directly to the culture dish) and neo-natal human dermal fibroblasts were added in culture medium. After 24 hours the medium and non-adherent cells were removed and replaced with fresh medium. Upon examination few cells were seen in association with the control fibers and no cells attached to untreated control fibers. By contrast, large numbers of cells attached to the inventively coated fibers and formed colonies along the fibers and spanning the space between the fibers. Indeed, nets of cells between fibers formed that showed contraction and drawing together of fibers.

Figure 3:
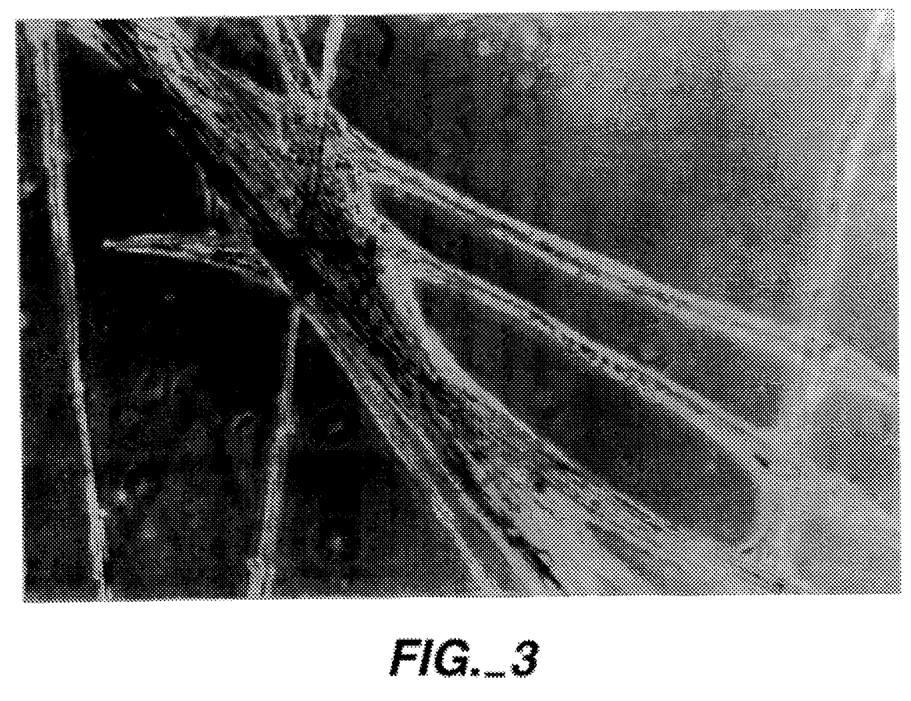
FIG. 3 is the photograph of polyglycolide fibers treated with an inventive peptide. Dermal fibroblasts were bonded to the fiber surfaces, and the cells commenced to grow and to form colonies.

This type of inventive embodiment is illustrative of tissue reconstruction materials, particularly for tissues such as ligaments, as is illustrated by FIG. 3 showing cell colonies spanning fibers.

In short, substantially all of the known biomaterials presently used or suggested for use as biomaterials can be readily adapted as the matrix component of the inventive composites and used for applications such as hard or soft tissue reconstructions, repair purposes, and in cell culture applications outside the body. For example, hydroxylapatite has been used to coat metal implants. Inclusion of inventive compounds into the coatings of hydroxylapatite should lead to a further ability of cells to attach to such coated implants. Yet further, silicone has been used for applications such as tendon repair or artificial blood vessels and other tissue prostheses, and inclusion or coatings of inventive compounds into or onto such materials or other biomaterials should be useful in body repair and reconstructive applications.

While composites of the invention are typically used in applications (both in the body and outside the body) for growing or promoting the growth of cells, another embodiment of this invention is to inhibit the migration of cells. For example, cells that are out of normal regulation processes (e.g., cancer and autoimmune situations) have an increased number of collagen receptors, which can be blocked by the inventive synthetic peptides due to competitive (and inhibitory) binding with respect to collagen. This aspect of the invention is illustrated by the following T-cell studies. Other implications for the T-cell aspects of this invention include drug delivery to infected T-cells with potential applications in AIDS therapy.

EXAMPLE 7

The interactions of T-lymphocytes with the extracellular matrix play an important role in their differentiation, maturation, and migration. Collagen is a major component of the physiological milieu in which T-cells reside, such as by affecting differentiation and migration behavior.

Mixed populations of peripheral blood CD4 and CD8 lymphocytes showed a strong affinity for substrates coated with rat tail type I collagen. Cultured T-cells were incubated in collagen-coated dishes in serum free medium, in the presence and absence of inventive peptides. The interactions between T-cells and collagen was markedly inhibited by inventive peptides (SEQ ID NOS. 1, 2, and 3). The maximal rate of T-cell binding was observed in the first 30 minutes in the absence of the inventive peptides. Inhibition was examined at several concentrations and times. Maximal inhibition by the peptides occurred at 30 minutes at 37° C. at a concentration of 35 μM. Thus, the molecular site on type I collagen involved in the interaction with T-cells appears to be the same as involved in fibroblast binding.

P-15 also induces metalloproteinases in dermal fibroblasts. This activity is useful for resolving fibrosis. In composites with hydroxyapatite, P-15 causes osteodifferentiation in non-osteoblastic (dermal) fibroblasts. This is confirmed by the induction of the following genes: type I collagen, collagenase, alkaline phosphatase, osteonectin, transforming growth factor β (TGF-β), and osteogenin (bone morphogenic protein, BMP-7). These studies confirm that the inventive peptides mimic the biological activity of collagen by binding to specific receptors and inducing biochemical processes characteristic of those induced by collagen itself.

In conditions such as arthritis, T-cells aggregate. Administration (such as by injection at the affected site) of the inventive peptides in a physiologically acceptable solution should prove efficacious. Administration (intravenous, intradermal, or subcutaneous) in amounts from about 1 to about 200 μK/kg body weight in combination with a pharmaceutically acceptable carrier, such as isotonic saline phosphate buffer solution or the like, should prove therapeutically useful. Pharmaceutically acceptable salts of the inventive peptides with organic and inorganic acids can be formed.

It is to be understood that while the invention has been described above in conjunction with preferred specific embodiments, the description and examples are intended to illustrate and not limit the scope of the invention, which is defined by the scope of the appended claims.

It is claimed:

1. An implant comprising:
   a matrix formed of a biomaterial and a peptide carried by the matrix, the peptide having enhanced cell binding with respect to collagen, the peptide having a domain that mimics collagen binding to cells, said domain including at least -Ile-Ala- folded in a β-bend at physiologic conditions, wherein the peptide has the sequence Gly-Thr-Pro-Gly-Pro-Gln-Gly-Ile-Ala-Gly-Gln-Arg-Gly-Val-Val (SEQ ID NO: 1), Gly-Pro-Gln-Gly-Ile-Ala-Gly-Gln-Arg (SEQ ID NO: 2), Gln-Gly-Ile-Ala-Gly-Gln (SEQ ID NO: 3), Gln-Gly-Ile-Ala-Gly-Gln-Arg (SEQ ID NO: 4), Phe-Gly-Ile-Ala-Gly-Phe (SEQ ID NO: 5), Gly-Ile-Ala-Gly-Gln (SEQ ID NO: 6), Gln-Gly-Ala-Ile-Ala-Gln (SEQ ID NO: 7), Phe-Gly-Ile-Ala-Gly-Phe (SEQ ID NO:9), Cys-Gly-Ile-Ala-Gly-Cys (SEQ ID NO:10), Glu-Gly-Ile-Ala-Gly-Lys (SEQ ID NO:11), NAc-Ile-Ala-Ala (SEQ ID NO:12), Ile-Ala-βAla (SEQ ID NO:13), and NAc-Ile-Ala-N-Me (SEQ ID NO:14).

2. The implant as in claim 1 wherein the peptide is in an amount effective to promote cell attachment, and the matrix has the peptide coated thereon.

3. The implant as in claim 2 wherein the matrix includes a ceramic, a metal, a polymer or a composite thereof.

4. The implant as in claim 1 or 2 wherein the matrix includes a hydrogel.

5. The implant as in claim 1 or 2 wherein the matrix is in the form of polymer fibers.

6. The implant as in claim 1 or 2 wherein at least part of the matrix is a soluble polymer or is a hydrogel.

7. The implant as in claim 1 wherein the peptide is bound to the matrix.

8. The implant as in claim 7 wherein the matrix has interstices.

\* \* \* \* \*

UNITED STATES PATENT AND TRADEMARK OFFICE
CERTIFICATE OF CORRECTION

PATENT NO. : 5,635,482
DATED : June 3, 1997
INVENTOR(S) : Rajendra S. Bhatnagar

It is certified that error appears in the above-indentified patent and that said Letters Patent is hereby corrected as shown below:

In Column 6, line 29:
    replace "stabilize the Q-fold.  Because the stabilizing hydrogen bond" with:

--stabilize the β-fold.  Because the stabilizing hydrogen bond--

Signed and Sealed this

Third Day of February, 1998

Attest:

BRUCE LEHMAN

Attesting Officer

Commissioner of Patents and Trademarks